United States Patent
Argentine et al.

(10) Patent No.: US 9,095,463 B2
(45) Date of Patent: Aug. 4, 2015

(54) STENT-GRAFT DELIVERY HAVING A TIP CAPTURE MECHANISM WITH ELONGATED CABLES FOR GRADUAL DEPLOYMENT AND REPOSITIONING

(71) Applicant: Medtronic Vascular, Inc., Santa Rosa, CA (US)

(72) Inventors: Jeffery Argentine, Santa Rosa, CA (US); Joshua Schmitt, Santa Rosa, CA (US); Mark Stiger, Santa Rosa, CA (US); Brandon Woll, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 66 days.

(21) Appl. No.: 13/773,152

(22) Filed: Feb. 21, 2013

(65) Prior Publication Data

US 2014/0236278 A1 Aug. 21, 2014

(51) Int. Cl.
*A61F 2/962* (2013.01)
*A61F 2/966* (2013.01)
*A61F 2/95* (2013.01)
*A61F 2/89* (2013.01)

(52) U.S. Cl.
CPC .............. *A61F 2/962* (2013.01); *A61F 2/966* (2013.01); *A61F 2/89* (2013.01); *A61F 2002/9534* (2013.01); *A61F 2002/9665* (2013.01)

(58) Field of Classification Search
None
See application file for complete search history.

(56) References Cited

U.S. PATENT DOCUMENTS

| | | |
|---|---|---|
| 2006/0155366 A1 | 7/2006 | Laduca et al. |
| 2006/0276872 A1 | 12/2006 | Arbefeuille et al. |
| 2009/0099640 A1* | 4/2009 | Weng ............................ 623/1.11 |
| 2009/0276027 A1 | 11/2009 | Glynn et al. |
| 2010/0168838 A1 | 7/2010 | Hartley et al. |
| 2010/0268317 A1* | 10/2010 | Stiger et al. ................... 623/1.12 |
| 2011/0144735 A1 | 6/2011 | Hartley et al. |
| 2011/0257718 A1 | 10/2011 | Argentine |
| 2011/0270371 A1 | 11/2011 | Argentine |
| 2011/0270372 A1 | 11/2011 | Argentine |

FOREIGN PATENT DOCUMENTS

WO    WO2011/163386    12/2011

* cited by examiner

*Primary Examiner* — Tuan V Nguyen

(57) ABSTRACT

Stent-graft delivery systems having a tip capture mechanism with a plurality of elongated cables that allow for gradual deployment and repositioning of a stent-graft prosthesis. The tip capture mechanism includes a guiding assembly, a distal tip assembly, and a plurality of cables. In a first relative position, the distal tip assembly extends the guiding assembly to temporarily constrain the distal ends of the cables and an intermediate portion of each cable constrains an endmost crown of the prosthesis. In this first relative position, tension on the cables may be selectively adjusted to allow for both gradual continuous radial expansion and contraction of the endmost crowns of the stent-graft prosthesis. In a second relative position, the distal tip assembly does not extend over the guiding assembly and thus does not constrain the distal ends of the cables, and thereby the cables do not constrain the endmost crowns.

12 Claims, 10 Drawing Sheets

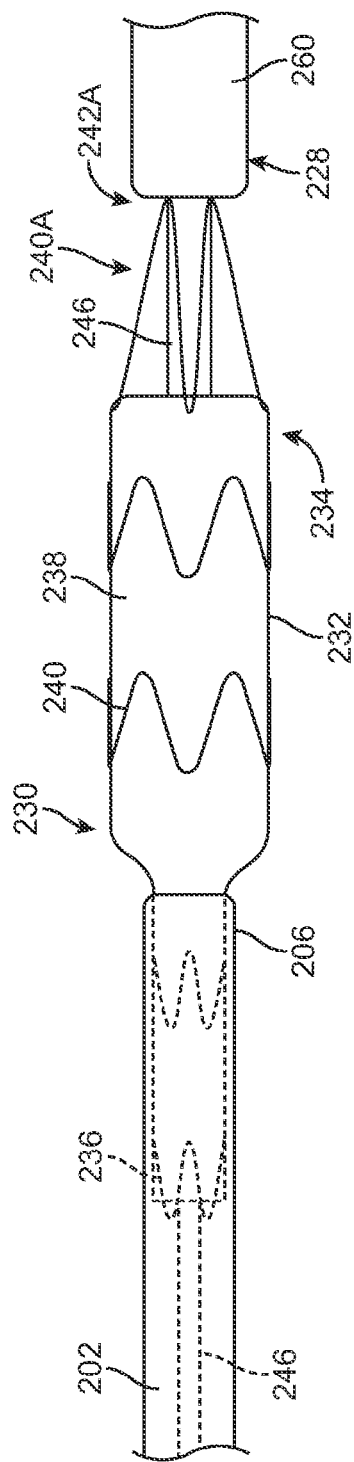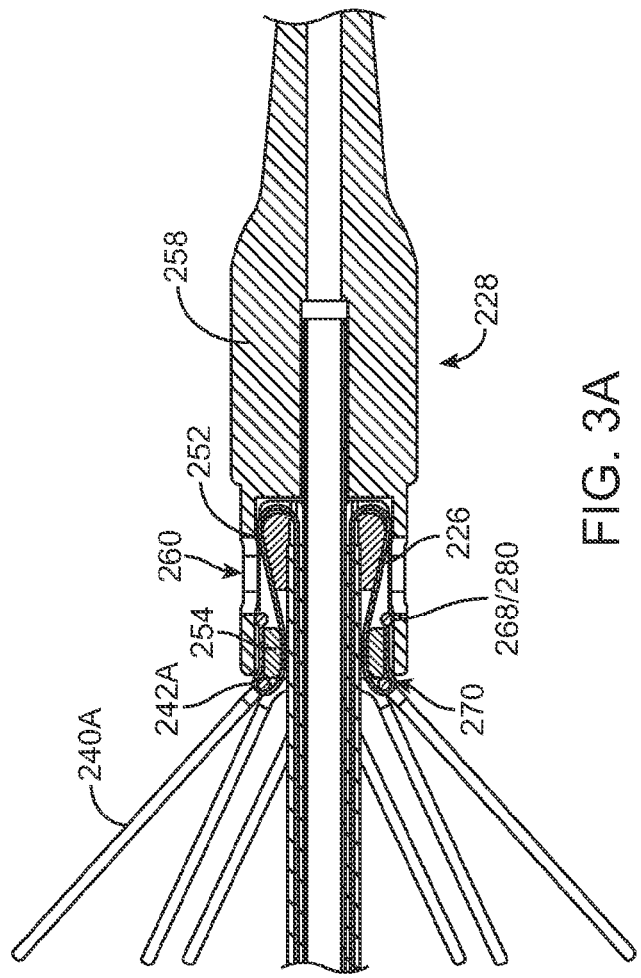
FIG. 3
FIG. 3A

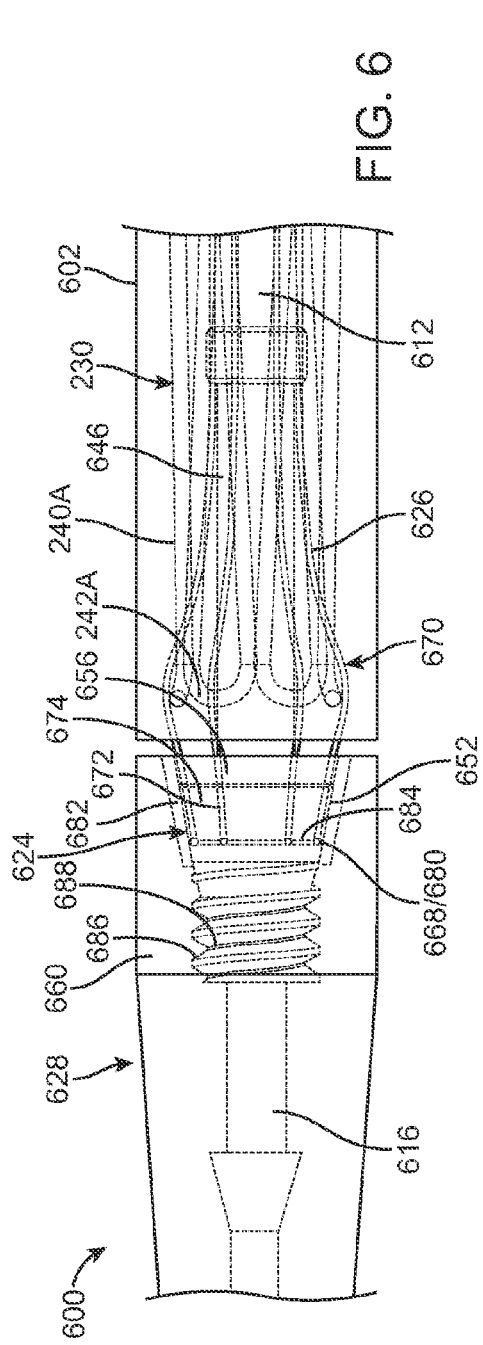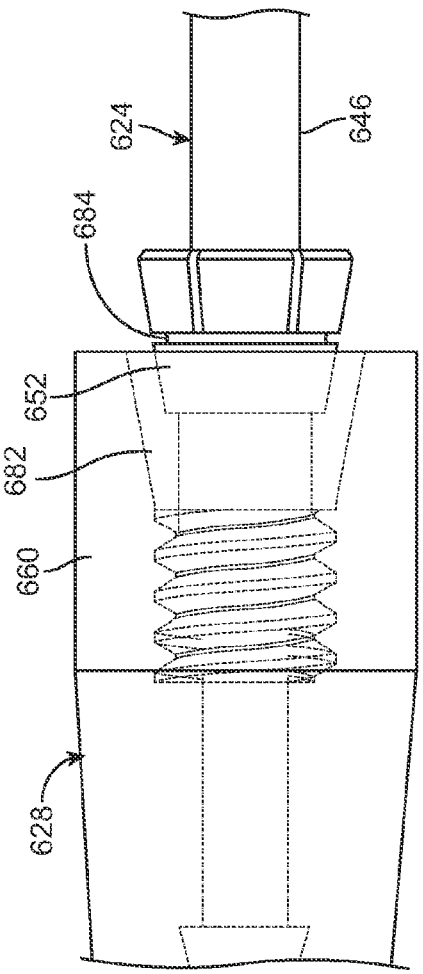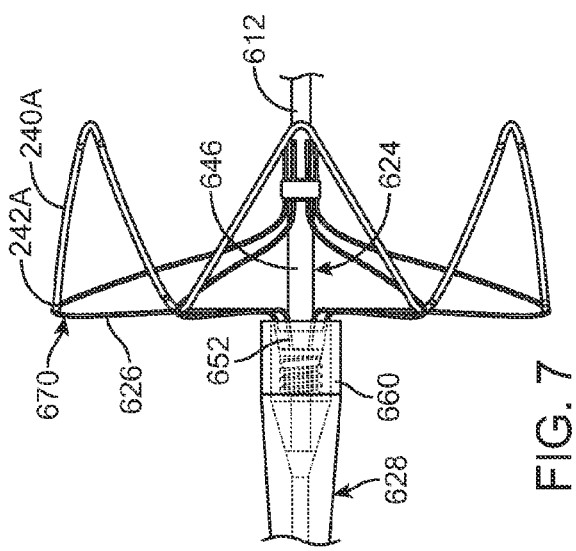

STENT-GRAFT DELIVERY HAVING A TIP CAPTURE MECHANISM WITH ELONGATED CABLES FOR GRADUAL DEPLOYMENT AND REPOSITIONING

FIELD OF THE INVENTION

The invention is related in general to implantable prostheses and in particular to self-expanding stent-grafts.

BACKGROUND OF THE INVENTION

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expandable stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts may be deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes arranged for relative axial movement. For example, a self-expanding stent-graft may be compressed and disposed within the distal end of an outer catheter tube distal of a stop fixed to the inner member. The catheter is then maneuvered, typically routed through a body lumen until the end of the catheter and the stent-graft are positioned at the intended treatment site. The stop on the inner member is then held stationary while the outer tube of the delivery catheter is withdrawn. The stop prevents the stent-graft from being withdrawn with the sheath. As the sheath is withdrawn, the stent-graft is released from the confines of the sheath and radially self-expands so that at least a portion of it contacts and substantially conforms to a portion of the surrounding interior of the lumen, e.g., the blood vessel wall or anatomical conduit.

In recent years, to improve optimal control and alignment during deployment and positioning of a stent-graft, various tip capture spindles have been incorporated into the delivery system utilized for percutaneously delivering the stent-graft prosthesis. Tip capture involves restraining the proximal end stent of the stent-graft in a radially compressed configuration in conjunction with the main body restraint achieved by other delivery system components, such as a tubular cover shaft or sheath. The tip capture spindle can be activated at any time during stent-graft deployment to suit any number of system characteristics driven by the therapy type, stent-graft type, or specific anatomical conditions that may prescribe the release timing. Typically, the tip capture release is activated after some or all the main stent-graft body release, and thus provides a mean of restraining the stent-graft during positioning and any re-positioning. Additional restraint of the stent-graft is a key characteristic when the operator is attempting to accurately position the stent-graft relative to an anatomical target. The tip capture restraint also aids in reducing an abrupt force of expansion when the stent-graft is released from the graft cover or sheath.

For example, U.S. Patent Application Publication No. 2006/0276872 to Arbefuielle et al. and U.S. Patent Application Publication No. 2009/0276027 to Glynn et al., both herein incorporated by reference in their entirety, describe tip capture mechanisms that restrain the proximal end stent of the stent-graft while the remainder of the stent-graft expands, then releases the proximal end stent. The proximal end stent (sometimes also referred to as the anchor stent) is attached to the graft material of the stent-graft so as to have an "open web" or "free flow" proximal end configuration in which the proximal endmost crowns thereof extend past or beyond the graft material such that the proximal endmost crowns are exposed or bare, and thus free to interact with a tip capture mechanism and couple the stent-graft prosthesis to the delivery system. FIGS. 1A and 1B illustrate a delivery system 10 having a tip capture spindle 12 designed to couple or interact with a stent-graft 14 having an open web or free flow proximal end configuration 16. More particularly, endmost crowns 18 engage or hook around retractable arms or retainer elements 20 of the tip capture spindle 12. Delivery system 10 includes at least three concentric shafts, namely an outer delivery sheath or graft cover 22, an intermediate shaft 24 coupled to tip capture spindle 12, and an elongate inner shaft 26 coupled to distal tip assembly 28. When graft cover 22 is retracted to allow stent-graft 14 to self-expand, endmost crowns 18 of the end stent 15 remain hooked around tip capture retainer elements 20, as shown in FIG. 1A. To release end stent 15, intermediate shaft 24 coupled to tip capture spindle 12 is retracted longitudinally relative to inner shaft 26 to retract tip capture spindle 12 such that end stent 15 is released from tip capture spindle 12 and allowed to self-expand, as shown in FIG. 1B. The Captivia Delivery System manufactured by Medtronic Vascular, Inc. of Santa Rosa, Calif. is one example of a delivery system having a tip capture mechanism as described above, which may be utilized for delivering endovascular stent-grafts such as the Valiant Thoracic Stent-graft manufactured by Medtronic Vascular, Inc. of Santa Rosa, Calif.

Tip capture mechanisms have improved accuracy of deployment of self-expanding stent-grafts. Embodiments hereof relate to improvements in delivery systems for gradual deployment and repositioning of the stent-graft.

BRIEF SUMMARY OF THE INVENTION

Embodiments hereof relate to a stent-graft delivery system including an elongate shaft, a guiding assembly disposed over the shaft, a distal tip assembly coupled to a distal end of the shaft, and a plurality of cables that extend over the elongate shaft. The distal tip assembly and the guiding assembly are moveable relative to each other. Each cable includes a first end, an intermediate portion configured to engage an endmost crown of a stent of a stent-graft prosthesis, and a second end that extends distally beyond the stent-graft prosthesis. In a first relative position of the distal tip assembly and the guiding assembly, a portion of the distal tip assembly extends over an outer surface of a distal portion of the guiding assembly and constrains the second ends of the cables between the outer surface of the distal portion of the guiding assembly and an inner surface of the portion of the distal tip assembly. In the first relative position of the distal tip assembly and the guiding assembly, tension on the cables may be selectively reduced for gradual continuous expansion of the endmost crowns of the stent or may be selectively increased for gradual continuous radial contraction of the endmost crowns of the stent. In a second relative position of the distal tip assembly and the guiding assembly, the distal tip assembly does not constrain the second ends of the cables.

Embodiments hereof also relate to a method of deploying a stent-graft prosthesis. A delivery system having a stent-graft prosthesis mounted on an elongate shaft is percutaneously advanced, wherein a guiding assembly is disposed over the shaft, a plurality of cables extend over the shaft and constrain endmost crowns of a stent of the stent-graft prosthesis, and a distal tip assembly is coupled to a distal end of the shaft, the distal tip assembly and the guiding assembly being moveable relative to each other. A portion of the distal tip assembly proximally extends over an outer surface of a distal portion of the guiding assembly to constrain second ends of the cables between an inner surface of the distal tip assembly and the outer surface of the distal portion of the guiding assembly. The stent-graft prosthesis is positioned and then partially deployed by retracting an outer sheath of the delivery system to expose at least a portion of the stent-graft prosthesis, wherein the portion of the stent-graft prosthesis self-expands and the endmost crowns of the stent remain constrained by the cables. The endmost crowns of the stent are partially deployed in a continuous gradual manner by reducing tension on the cables, wherein reducing tension allows the endmost crowns to partially radially expand while the cables continue to constrain the endmost crowns of the stent. To fully deploy the stent-graft prosthesis, the distal tip assembly or the guiding assembly is moved such that the distal tip assembly does not constrain the second ends of the cables.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3 is a side view of a distal portion of the stent-graft delivery system of FIG. 2, wherein the stent-graft is in a partially deployed configuration in which a portion of the body of the stent-graft is deployed or radially expanded.

FIG. 3A is a sectional view of a portion of FIG. 3 taken along the line A-A of FIG. 3.

FIG. 6 is a side perspective view of a distal portion of a stent-graft delivery system having a tip capture mechanism according to another embodiment hereof, wherein a stent-graft prosthesis mounted on the delivery system is in a delivery configuration.

FIG. 7 is a side perspective view of a distal portion of the stent-graft delivery system of FIG. 6, wherein the stent-graft is in a fully deployed configuration with the endmost crowns of the stent-graft captured via the tip capture mechanism.

FIG. 8 is a perspective view of a distal portion of the stent-graft delivery system of FIG. 6, wherein the stent-graft is in a fully deployed configuration with the endmost crowns of the stent-graft released from the tip capture mechanism.

DETAILED DESCRIPTION OF THE INVENTION

Specific embodiments of the present invention are now described with reference to the figures, wherein like reference numbers indicate identical or functionally similar elements. Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft prosthesis "proximal" is the portion nearer the heart by way of blood flow path while "distal" is the portion of the stent-graft further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as the aorta, coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1A:
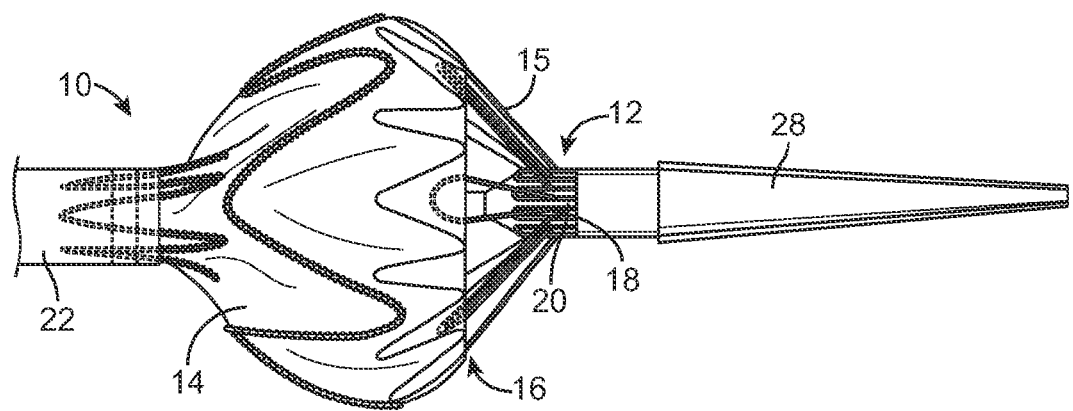
FIGS. 1A and 1B are side views of a distal end of a delivery system having a tip capture spindle designed to couple or interact with a stent-graft having an open web or free flow proximal end configuration.
Figure 1B:
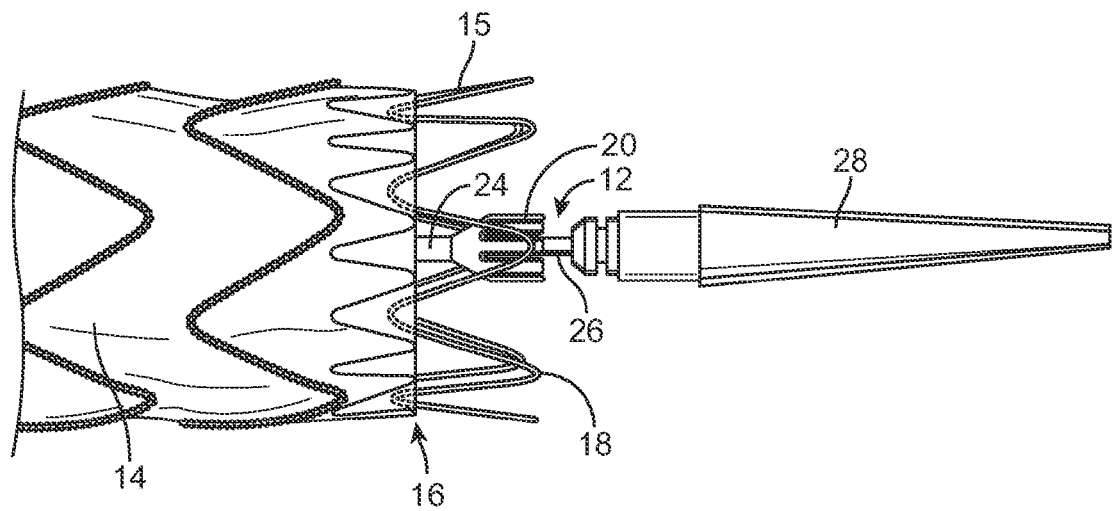
Figure 2:
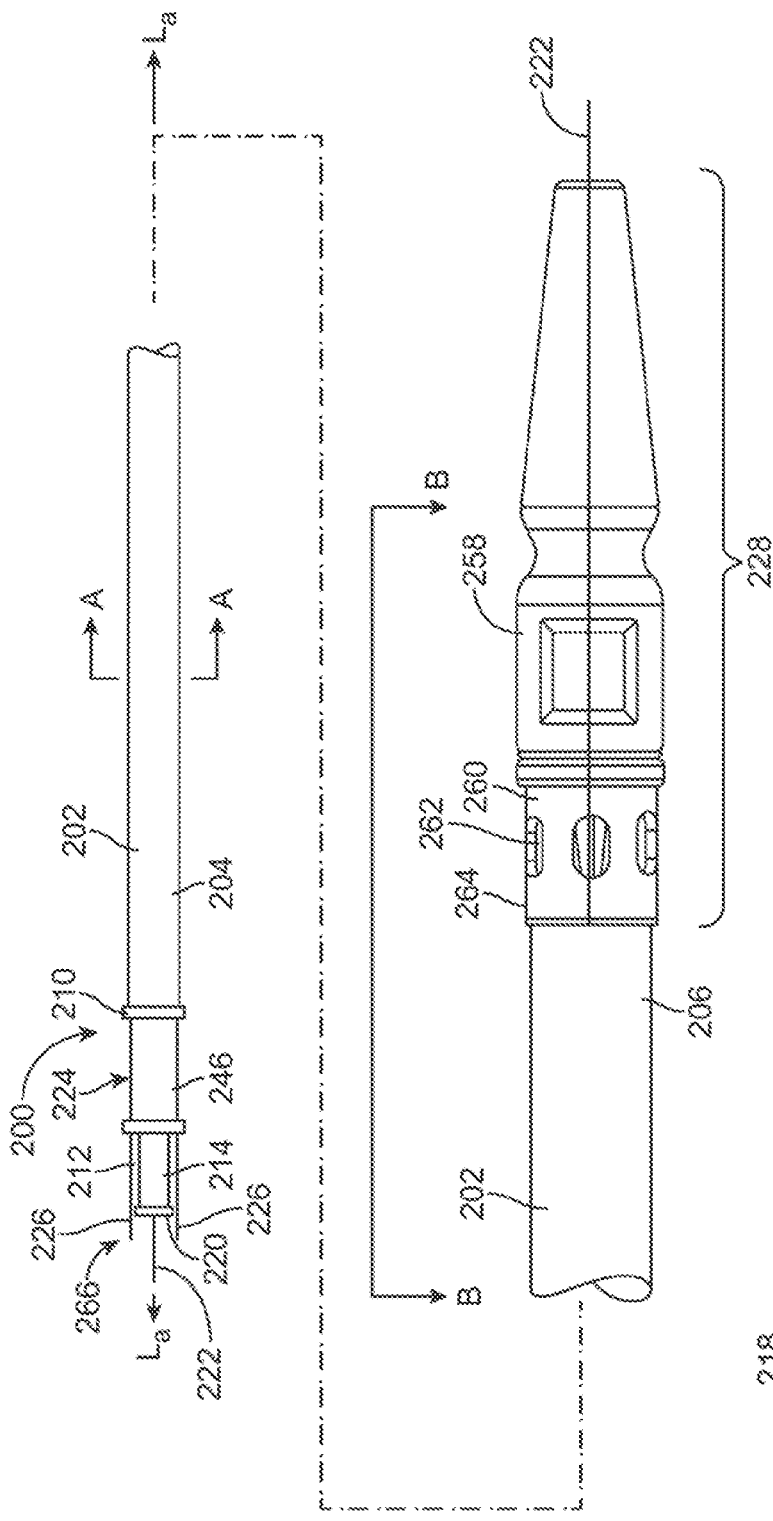
FIG. 2 is a side view of a stent-graft delivery system having a tip capture mechanism according to an embodiment hereof, wherein a stent-graft prosthesis mounted on the delivery system is in a delivery configuration.
Figure 2A:
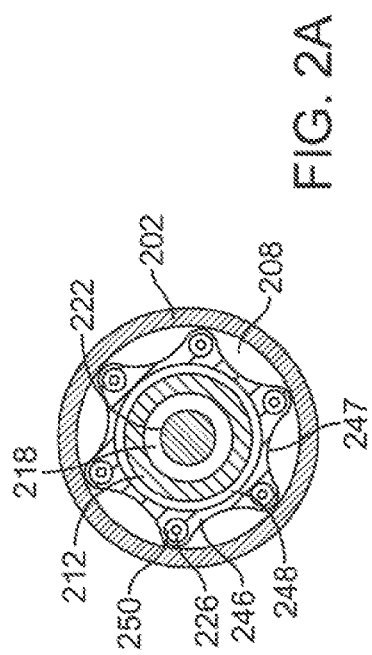
FIG. 2A is a cross-sectional view taken along the line A-A of FIG. 2.
Figure 2B:
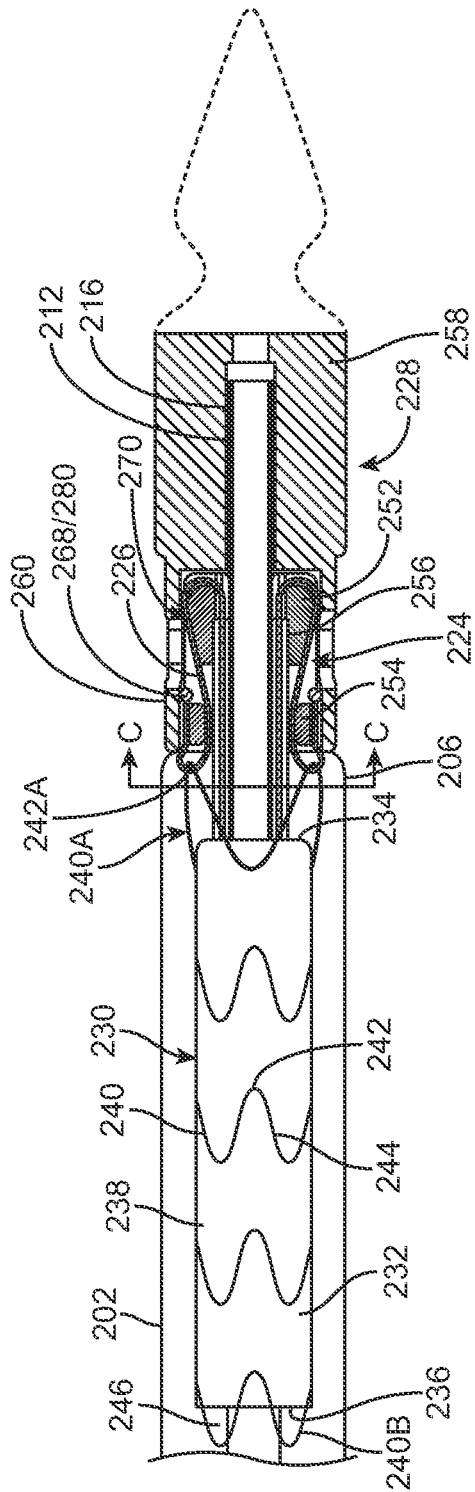
FIG. 2B is a cross-sectional view taken along the line B-B of FIG. 2.
Figure 2C:
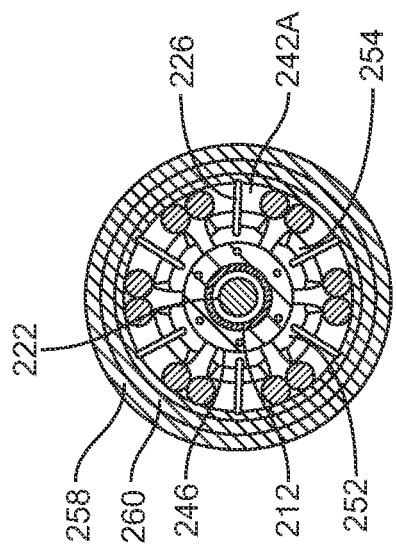
FIG. 2C is a cross-sectional view taken along the line C-C of FIG. 2B.
Figure 2D:
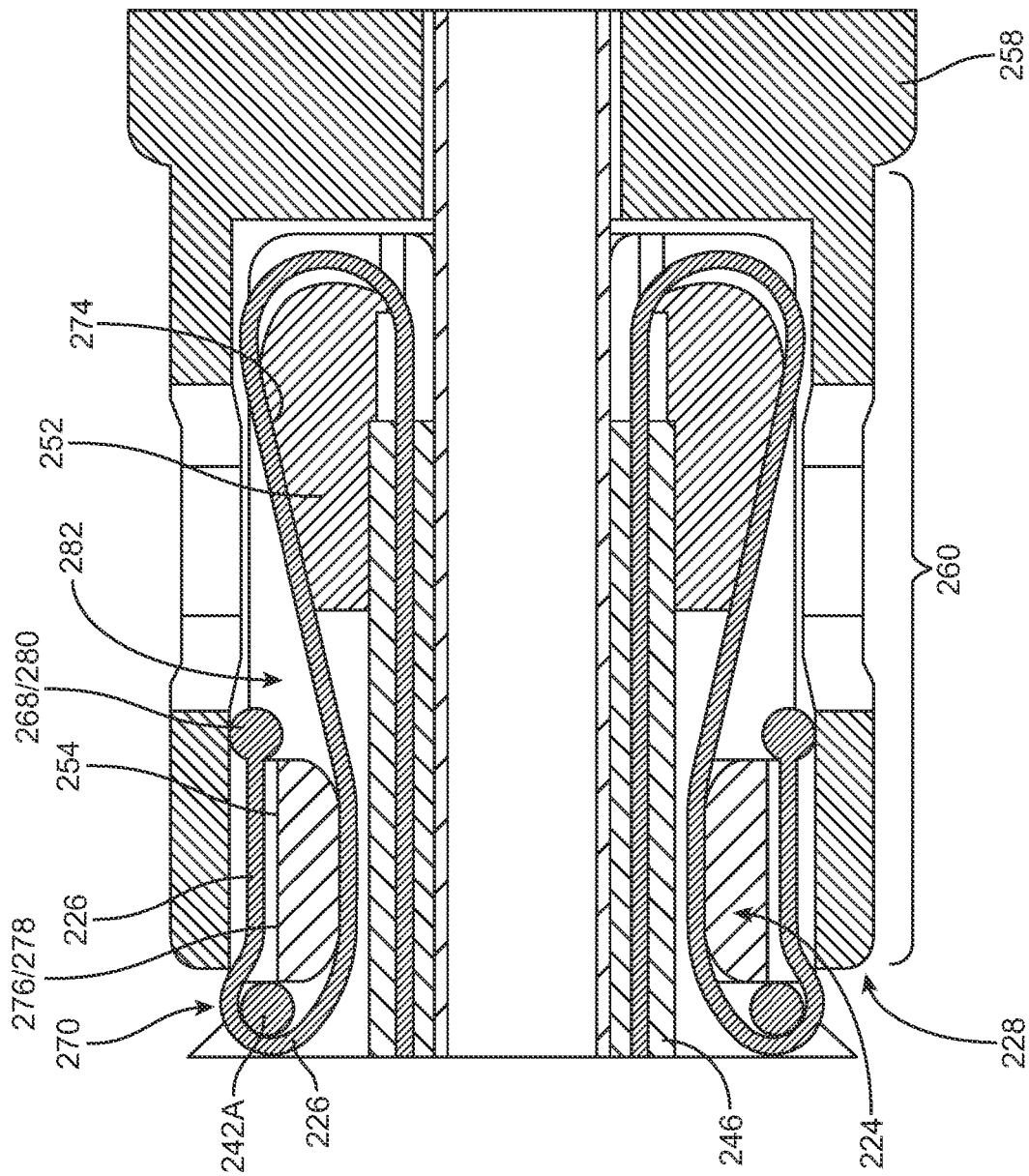
FIG. 2D is an enlarged view of a portion of FIG. 2B.
Figure 2E:
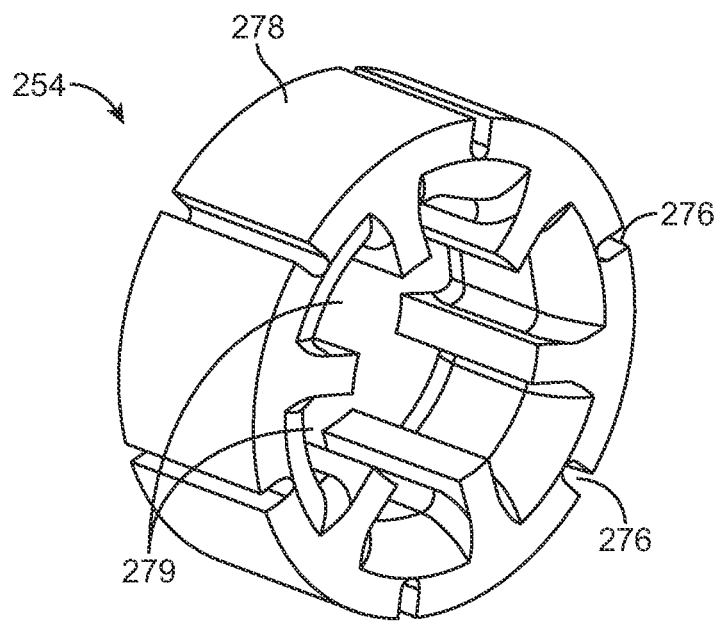
FIG. 2E is a perspective view of a component of a guiding assembly of FIG. 2 removed from the stent-graft delivery system for illustrative purposes only.
Figure 2F:
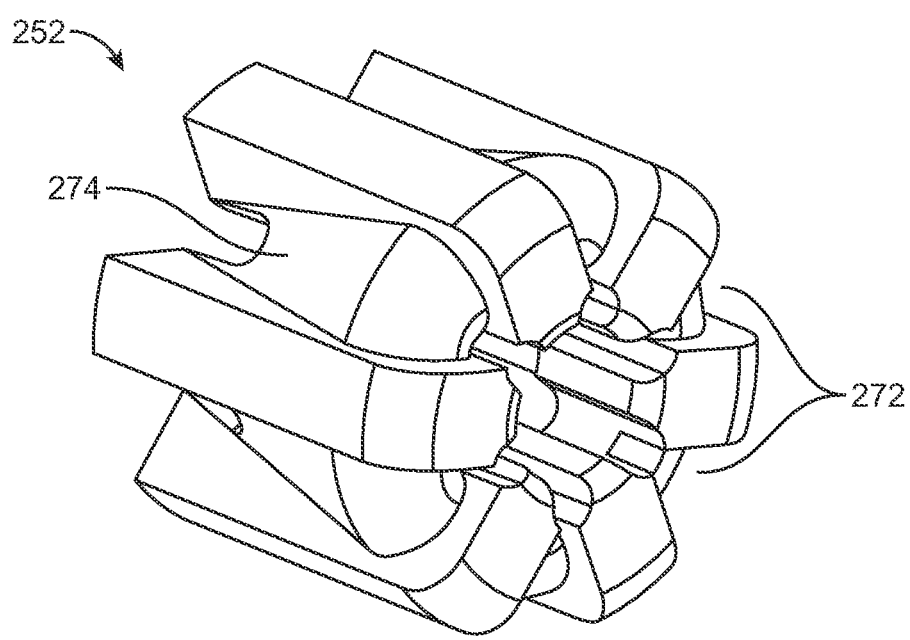
FIG. 2F is a perspective view of another component of the guiding assembly of FIG. 2 removed from the stent-graft delivery system for illustrative purposes only.
Figure 4:
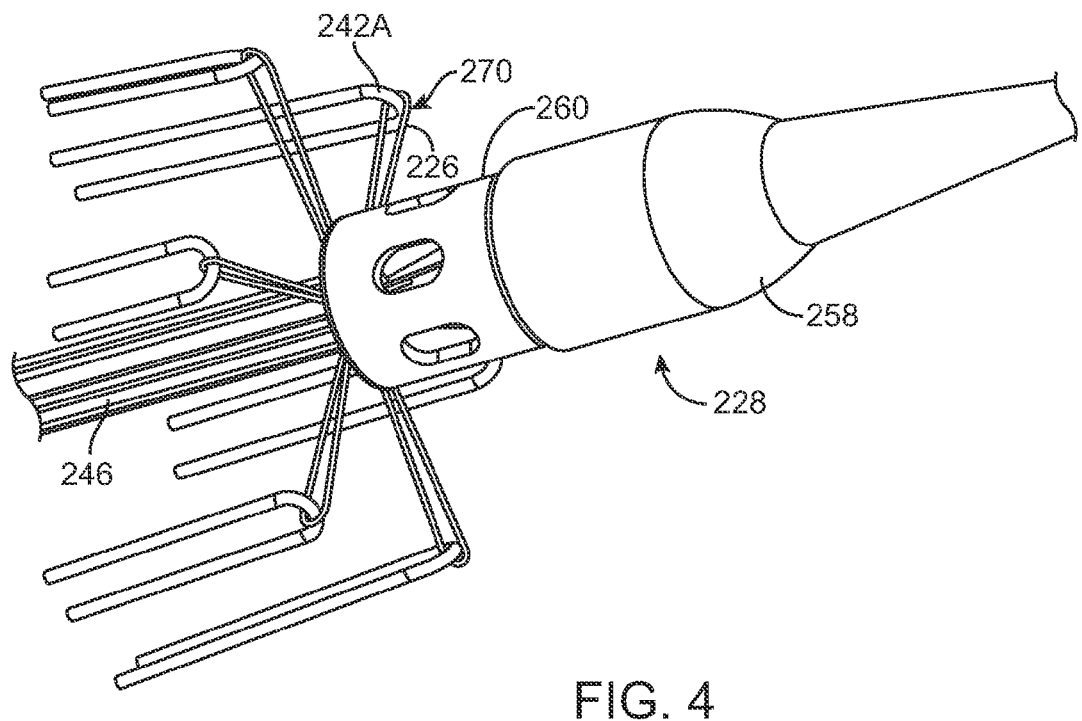
FIG. 4 is a perspective view of a distal portion of the stent-graft delivery system of FIG. 2, wherein the body of stent-graft is deployed or radially expanded with the endmost crowns of the stent-graft captured via the tip capture mechanism.
Figure 4A:
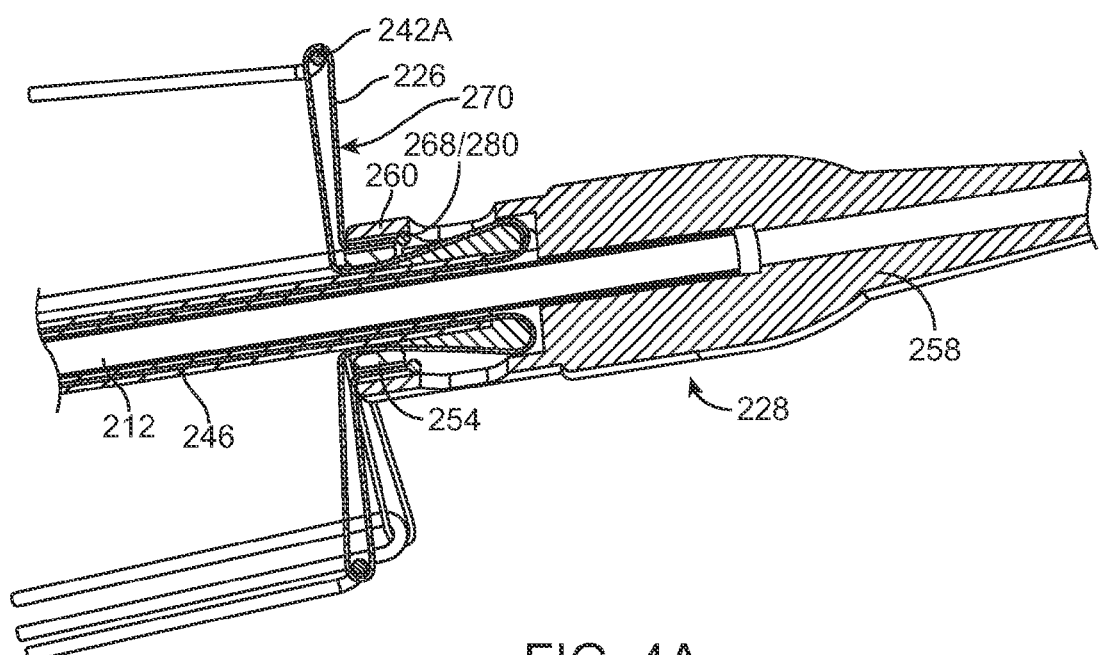
FIG. 4A is a sectional view taken along the line A-A of FIG. 4.
Figure 5:
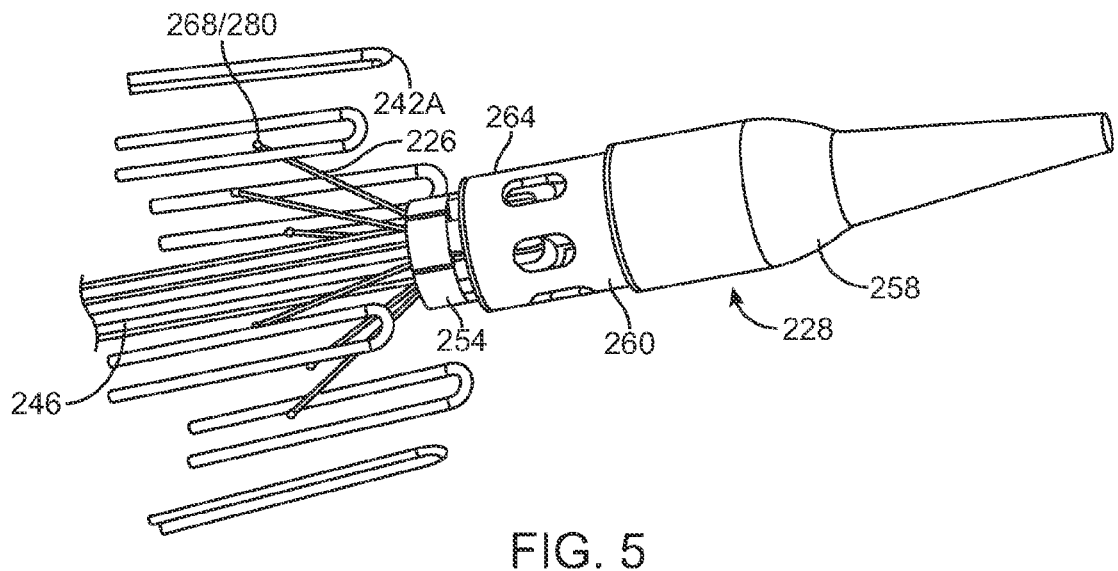
FIG. 5 is a perspective view of a distal portion of the stent-graft delivery system of FIG. 2, wherein the stent-graft is in a fully deployed configuration with the endmost crowns of the stent-graft released from the tip capture mechanism.
Figure 5A:
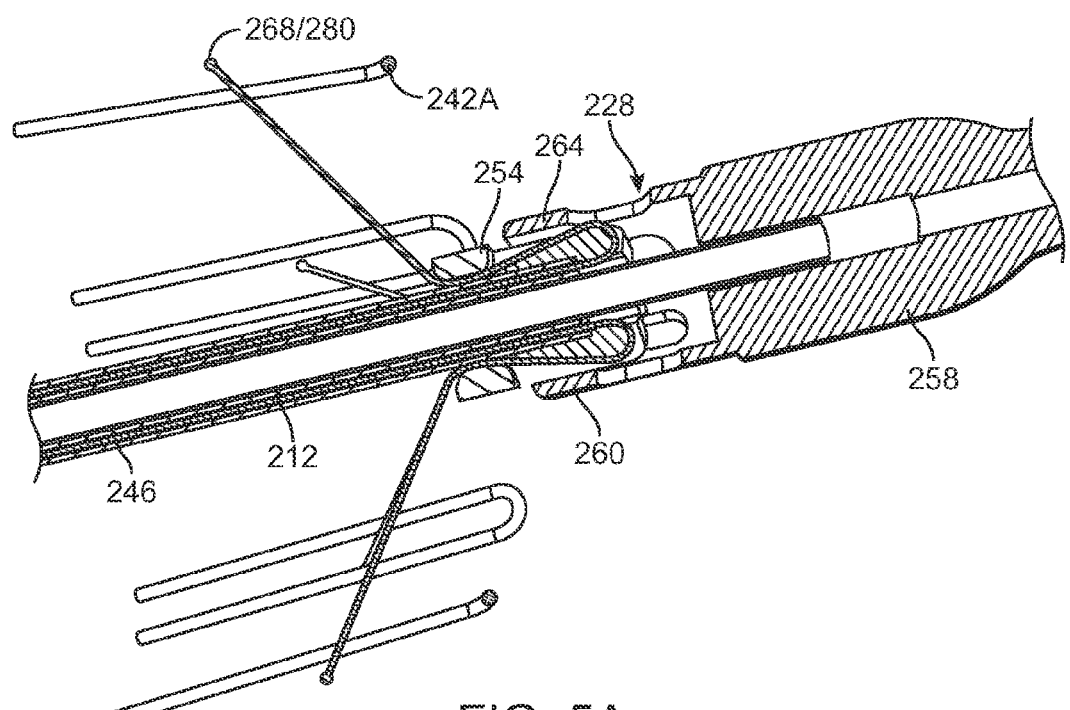
FIG. 5A is a sectional view of taken along the line A-A of FIG. 5.

Embodiments hereof relate to stent-graft delivery systems having a tip capture mechanism with a plurality of elongated cables that allows for partial or gradual deployment and repositioning of the stent-graft prosthesis. Tension on the cables may be selectively adjusted to allow for both gradual continuous radial expansion and contraction of endmost crowns of the stent-graft prosthesis while the stent-graft prosthesis is being positioned in situ as desired. More particularly, according to an embodiment hereof, a delivery system 200 having a tip capture mechanism to allow for partial deployment and repositioning of a stent-graft prosthesis 230 is shown and described with respect to FIGS. 2-5. FIGS. 2, 2A, 2B, and 2C illustrate delivery system 200 for delivering a self-expanding stent-graft prosthesis 230 within a vasculature, wherein stent-graft prosthesis 230 is in a compressed delivery configuration. FIG. 2 is a schematic side view of system 200, while FIG. 2A is a cross-sectional view taken along line A-A of FIG. 2, FIG. 2B is a sectional view taken along line B-B of FIG. 2, FIG. 2C is a cross-sectional view taken along line C-C of FIG. 2B, and FIG. 2D is an enlarged view of a portion of FIG. 2B. FIG. 2E and FIG. 2F are perspective views of components of the guiding assembly removed from the delivery system for illustrative purposes only. FIGS. 3 and 3A illustrate a distal portion of delivery system 200 with stent-graft prosthesis 230 in a partially deployed configuration in which the body of the stent-graft prosthesis is radially expanded but the endmost crowns of the stent-graft prosthesis are not radially expanded. FIGS. 4 and 4A illustrate a distal portion of delivery system 200 with endmost crowns of the stent-graft prosthesis 230 in a partially deployed or radially expanded configuration but still captured via the tip capture mechanism. FIGS. 5 and 5A illustrate a distal portion of delivery system 200 with stent-graft prosthesis 230 in a fully deployed configuration with the endmost crowns of the stent-graft released from the tip capture mechanism.

Stent-graft delivery system 200 includes an elongate inner shaft 212 having a handle 220 coupled to a proximal end 214 thereof and a distal tip assembly 228 coupled to a distal end 216 thereof (shown in FIG. 2B), a plurality of elongate cables 226 that releasably couple stent-graft prosthesis 230 to delivery system 200, a guiding assembly 224 slidingly disposed over inner shaft 212 for guiding and directing cables 226, and an outer sheath or graft cover 202 sliding disposed over guiding assembly 224 to retain stent-graft prosthesis 230 in a constrained or compressed diameter configuration while the delivery system is tracked through a body lumen to the deployment site. With reference to FIG. 2B, stent-graft prosthesis 230 includes a tubular graft 232 having a first edge or end 234, a second edge or end 236, and a body 238 there between which defines a lumen (not shown) through stent-graft prosthesis 230. In an embodiment, first end 234 of graft 232 may be referred to as a proximal end of graft 232 and a proximal end of stent-graft prosthesis 230, which is conventionally the end that is coupled to a tip capture mechanism of a delivery system, and second end 236 of graft 232 may be referred to as a distal end of graft 232 and a distal end of stent-graft prosthesis 230. Graft 232 may be formed from any suitable graft material, for example and not limited to, a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa. Stent-graft prosthesis 230 also includes at least one radially-compressible stent or scaffold 240 that is coupled to graft 232 for supporting the graft material and that is operable to self-expand into apposition with an interior wall of a body vessel (not shown). In the embodiment depicted in FIG. 2B, stent-graft prosthesis 230 includes a series of five independent or separate cylindrical stents 240. Each stent 240 is constructed from a self-expanding or spring material, such as Nitinol, and is a sinusoidal patterned ring including a plurality of crowns or bends 242 and a plurality of struts or straight segments 244 with each crown being formed between a pair of opposing struts. Although shown with five stents 240, it will be understood by those of ordinary skill in the art that stent-graft prosthesis 230 may include a greater or smaller number of stents 240 depending upon the desired length of stent-graft prosthesis 230 and/or the intended application thereof. For description purposes only, the stent that is coupled adjacent and proximate to first end 234 of graft 232 is referred to herein as first end stent 240A and the stent that is coupled adjacent and proximate to second end 236 of graft 232 is referred to herein as second end stent 240B but it will be understood by those of ordinary skill in the art that all of the stents may have identical or different patterns or configurations. Stents 240 are coupled to graft 232 by stitches or other means known to those of skill in the art. In the embodiment shown in FIG. 2, stents 240 are coupled to an outer surface of graft 232. However, stents 240 may alternatively be coupled to an inside surface of graft 232. When stent-graft prosthesis 230 is used for treating an aneurysm, stents 240 have sufficient radial spring force and flexibility to conformingly engage stent-graft prosthesis 230 with the body lumen inner wall, to avoid excessive leakage, and prevent pressurization of the aneurysm, i.e., to provide a leak-resistant seal. Although some leakage of blood or other body fluid may occur into the aneurysm isolated by stent-graft prosthesis 230, an optimal seal will reduce the chances of aneurysm pressurization and resulting rupture.

In the compressed delivery configuration of FIG. 2 and FIG. 2B, stent-graft prosthesis 230 is mounted over a multi-lumen shaft 246 of guiding assembly 224 and graft cover 202 extends over multi-lumen shaft 246 to retain stent-graft prosthesis 230 in the compressed diameter configuration. Multi-lumen shaft 246 is described in more detail herein. In FIG. 2 and FIG. 2B, graft cover 202 is in a non-retracted, delivery configuration. Graft cover 202 defines a lumen 208 extending from a proximal end 204 to a distal end 206. Graft cover 202 is movable in an axial direction along and relative to multi-lumen shaft 246 and extends to a proximal portion of the graft delivery system where it may be controlled via an actuator, such as a handle 210 to selectively expand the stent-graft prosthesis 230 disposed around multi-lumen shaft 246. Handle 210 may be a push-pull actuator that is attached or connected to a proximal end 204 of graft cover 202. Alternatively, the actuator may be a rotatable knob (not shown) that is attached or connected to proximal end 204 of graft cover 202 such that when the knob is rotated, graft cover 202 is retracted in a proximal direction to expand the graft. Alternatively, the actuator may use a combination of rotation and sliding to retract graft cover 202, as described, for example, in U.S. Pat. No. 7,419,501 to Shiu et al., U.S. Patent Publication No. 2011/0257718 to Argentine, U.S. Patent Publication No. 2011/0270371 to Argentine, and U.S. Patent Publication No. 2011/0270372 to Argentine, each of which is incorporated by reference herein. Thus, when the actuator is operated, i.e., manually turned or pulled, graft cover 202 is proximally retracted over inner shaft 212 in a proximal direction. Graft cover 202 may be constructed of any suitable flexible polymeric material, including but not limited to polyethylene terephalate (PET), nylon, polyethylene, PEBAX, or combinations thereof, either blended or co-extruded.

Inner shaft 212 may be constructed from a flexible metal tube of NiTi (Nitinol™), stainless steel, or the like, or may be constructed of a rigid plastic tube of PEEK polyetheretherketone, polyimide, or the like. Inner shaft 212 may define a guidewire lumen 218 for receiving a guidewire 222 there through. Alternatively, inner shaft 212 may instead be a solid rod (not shown) without a lumen extending there through. In an embodiment where inner shaft 212 is a solid rod, inner shaft 212 is tracked to the target site with the assistance of a tapered and flexible nosecone 258 of distal tip assembly 228. Distal tip assembly 228 also includes a sleeve portion 260 which proximally extends from nosecone 258 and functions in the deployment of stent-graft prosthesis 230, as will be described in more detail herein. A proximal end of sleeve portion defines a proximal end 264 of distal tip assembly 228. Those skilled in the art will appreciate that nosecone 258 and sleeve portion 260 of distal tip assembly 228 can be formed as a single unit and/or assembled from individual parts or components. Suitable materials for distal tip assembly 228 include Pebax, urethane, silicone, other flexible polymers, and the like, any of which may also include a radiopaque additive to provide the clinician with a visible tip when using fluoroscopy guidance to deliver the stent-graft within the patient.

Guiding assembly 224 includes elongate multi-lumen sheath or shaft 246 which defines a main or central lumen 248 such that multi-lumen shaft 246 may be slidingly disposed over inner shaft 212 as shown in the cross-sectional view of FIG. 2A. Multi-lumen shaft 246 may be constructed of any suitable flexible polymeric material, including but not limited to polyethylene terephalate (PET), nylon, polyethylene, PEBAX, or combinations thereof, either blended or co-extruded. In another embodiment hereof, multi-lumen shaft 246 may be constructed from a stainless steel spiral cut shaft or tube. In addition to central lumen 248, multi-lumen shaft 246 also defines a plurality of lumens 250 therethrough which are concentrically disposed around central lumen 248. In an embodiment, although not required, an outer surface 247 of multi-lumen shaft 246 is generally bumpy or wavy to minimize the amount of material between lumens 250 and therefore increase flexibility of multi-lumen shaft 246 as well as to increase lumenal space between multi-lumen shaft 246 and graft cover 202 for any desired fluid flow and/or folding of graft 232 of stent-graft prosthesis 230 during delivery. Alternatively, multi-lumen shaft 246 may be cylindrical with a smooth outer surface. The number of lumens 250 is equal to the number of cables 226, which is equal to the number of endmost crowns 242A of stent-graft prosthesis 230, and each lumen 250 is sized to slidingly receive a cable therethrough. Although shown with six cables 226, it will be understood by those of ordinary skill in the art that a greater or smaller number of cables may be used depending upon the number of end-most crowns 242A and the size of stent-graft prosthesis 230. Each cable 226 is an elongated strand of material that includes a first or proximal end 266 which extends to a proximal end of the delivery system (shown in FIG. 2) and a second or distal end 268 which extends distally beyond stent-graft prosthesis 230 (shown in FIGS. 2B and 2D). Exemplary materials for cables 226 include but are not limited to a monofilament or plastic suture material, such as polypropylene. As will be described in more detail, an intermediate portion 270 of each cable 226 loop or hook around and constrain endmost crowns 242A of stent-graft prosthesis 230, thereby temporarily or releasably coupling the stent-graft prosthesis to the delivery system in the delivery configuration shown in FIG. 2B and FIG. 2C.

In addition to multi-lumen shaft 246, guiding assembly 224 also includes a guiding component 252 and an annular stop 254 formed or disposed over a distal end 256 of multi-lumen shaft 246. Guiding component 252 and an annular stop 254 extend circumferentially around multi-lumen shaft 246 and are first shown in the sectional views of FIG. 2B and FIG. 2C. Annular stop 254 and guiding component 252 are shown removed from the delivery system for illustrative purposes in FIG. 2E and FIG. 2F, respectively. In a first relative position of guiding assembly 224 and distal tip assembly 228 depicted in FIG. 2B, sleeve portion 260 of distal tip assembly 228 extends over guiding component 252 and annular stop 254 and thereby constrains distal ends 268 of cables 226 as will be described in more detail herein. Those skilled in the art will appreciate that guiding component 252 and an annular stop 254 of guiding assembly 224 can be formed as a single unit and/or assembled from individual parts or components. Suitable materials for guiding component 252 and an annular stop 254 include Pebax, nylon, acrylonitrile butadiene styrene (ABS), polycarbonate, and similar polymers as well as metallic materials such as stainless steel.

With reference to FIGS. 2B-2F, grooves or channels 272 are formed on an inclined or tapered outer surface 274 of guiding component 252 for receiving intermediate portions 270 of cables 226. In addition, grooves or channels 276 are formed on an outer surface 278 of annular stop 254 for receiving intermediate portions 270 of cables 270. In the first relative position of guiding assembly 224 and distal tip assembly 228, grooves 272 and 276 of guiding component 252 and annular stop 254, respectively, hold or receive intermediate portions 270 of cables 226 which are wound around the guiding component and annular stop. More particularly, cables 226 extend through and exit out of lumens 250 of multi-lumen shaft 246. Cables 226 radially extend around a distal end of guiding component 252 and then longitudinally extend in a proximal direction within grooves 272 on tapered outer surface 274 of guiding component 252. The generally rounded distal end of guiding component 252 as well as the taper or incline of outer surface 274 directs or guides the cables 226 to annular stop 254 and helps to prevent kinking and/or tangling of cables 226. The degree or angle of the taper or incline of outer surface 274 may vary from that shown to accommodate different design configurations and applications. Cables 226 then extend within or through grooves or channels 279 formed on an inner surface of annular stop 254. Cables 226 then radially extend or loop around endmost crowns 242A of stent-graft prosthesis 230, which are adjacent to or abut against a proximal end of annular stop 254. Cables 226 then longitudinally extend in a distal direction within grooves 276 on outer surface 278 of annular stop 254. Distal ends 268 of cables 226, which include balls or spheres 280 attached thereto or integrally formed therewith, are constrained or wedged within a space or gap 282 formed between a distal end of annular stop 254, tapered outer surface 274 of guiding component 252, and an inner surface of sleeve portion 260 of distal tip assembly 228. Spheres 280 have a diameter greater than the diameter or width of cables 226, and the diameter of spheres 280 is greater than the width of grooves 276 on an outer surface 278 of annular stop 254 so that the spheres cannot pass through the grooves 276 of the annular stop. Accordingly, with the distal ends of cables 226 constrained or wedged between annular stop 254 and guiding component 252 and covered by distal assembly 228, intermediate portions 270 of cables 226 loop or hook around endmost crowns 242A of stent-graft prosthesis 230 to firmly or securely pull the stent-graft prosthesis against annular stop 254. Tension is applied to proximal ends 266 of cables 226 such that cables 226 are generally taut and intermediate portions 270 of cables 226 hold endmost crowns 242A securely or firmly against annular stop 254. In an embodiment, sleeve portion 260 includes a plurality of holes 262 (see FIG. 2) which provide access to intermediate portions 270 of cables 226 during assembly.

When initial or partial deployment of prosthesis 230 is desired, graft cover 202 is partially retracted to allow at least a portion of body 238 of prosthesis 230 to self-expand as shown in FIGS. 3 and 3A. Body 238 of stent-graft prosthesis 230 is permitted to expand while endmost crowns 242A of first or proximal stent 240A remain firmly or securely pulled against annular stop 254 via intermediate portions 270 of cables 226 as shown in FIG. 3A. Distal tip assembly 228 and guiding assembly 224 are still in the first relative position in which sleeve portion 260 of distal tip assembly 228 extends over a distal portion of guiding assembly 224, i.e., guiding component 252 and annular stop 254, to constrain distal ends 268 of cables 226. With endmost crowns 242A of stent-graft prosthesis 230 still coupled to delivery system 200 via cables 226, the stent-graft prosthesis may be repositioned if desired. In the embodiment depicted in FIG. 3, graft cover 202 is partially retracted such that distal end 206 thereof no longer covers or constrains proximal or first end 234 of prosthesis 230 and no longer covers at least a portion of body 238, thereby allowing proximal or first end 234 of prosthesis 230 to self-expand except as constrained by cables 226. However, in the embodiment of FIG. 3, graft cover 202 still constrains distal or second end 236 of prosthesis 230. This permits easier repositioning of prosthesis 230 than if graft cover 202 is retracted such that distal end 206 thereof no longer covers distal or second end 236 of prosthesis 230. However, in another embodiment hereof (not shown), graft cover 202 may be retracted such that distal end 206 no longer covers and radially constrains distal or second end 236 of prosthesis 230. In either embodiment, at some point, normally after all repositioning is completed, graft cover 202 is fully retracted such that distal end 206 of graft cover 202 no longer covers or constrains distal or second end 236 of prosthesis 230, thereby allowing distal or second end 236 to fully expand.

With distal tip assembly 228 and guiding assembly 224 still in the first relative position in which sleeve portion 260 of distal tip assembly 228 extends over a distal portion of guiding assembly 224 to constrain distal ends 268 of cables 226, tension on cables 226 may be selectively adjusted via proximal ends 266 thereof (see FIG. 2) to allow for gradual continuous radial expansion and/or contraction of endmost crowns 242A of stent-graft prosthesis 230. More particularly, with reference to FIG. 4 and FIG. 4A, endmost crowns 242A of stent-graft prosthesis 230 are radially expanded or deployed in a continuous gradual manner by reducing tension on cables 226. Intermediate portions 270 of cables 226 are still looped or hooked around endmost crowns 242A but the endmost crowns are no longer pulled against annular stop 254. Rather, by reducing the tension of cables 226, endmost crowns 242A are permitted to radially self-expand and the endmost crowns are radially spaced apart from guiding assembly 224 of delivery system 200. If any repositioning is desired, endmost crowns 242A may be radially contracted towards or back to the position shown in FIG. 3 and FIG. 3A by increasing the tension of cables 226.

After any and all repositioning is performed and stent-graft prosthesis 230 is positioned as desired, endmost crowns 242A of stent-graft prosthesis 230 may be fully deployed and released from delivery system 200 via movement of distal assembly 228. More particularly, in order to fully deploy the stent-graft prosthesis, inner shaft 212 and distal tip assembly 228 coupled thereto are distally advanced relative to guiding assembly 224 until distal tip assembly 228 and guiding assembly 224 are in a second relative position in which sleeve portion 260 of distal tip assembly 228 does not extend over a distal portion of guiding assembly 224 and does not constrain distal ends 268 of cables 226. Stated another way, inner shaft 212 and distal tip assembly 228 coupled thereto are distally advanced until distal ends 268 of cables 226 are proximal to proximal end 264 of distal tip assembly 228. As shown in FIG. 5 and FIG. 5A, distal ends 268 of cables 226 are exposed or no longer covered by distal tip assembly 228 and thus cables 226 release or are removed from endmost crowns 242A of stent-graft prosthesis 230 by pulling on proximal ends 266 of cables 226. As such, the stent-graft prosthesis is no longer coupled to delivery system 200 and the delivery system may then be removed from the patient, leaving stent-graft prosthesis 230 deployed in situ. Although final deployment of the stent-graft prosthesis is described via distal advancement of distal tip assembly 228, it would be understood by those of ordinary skill in the art that the required relative movement between distal tip assembly 228 and guiding assembly 224 may be accomplished via proximal retraction of the guiding assembly 224.

Figure 6A:
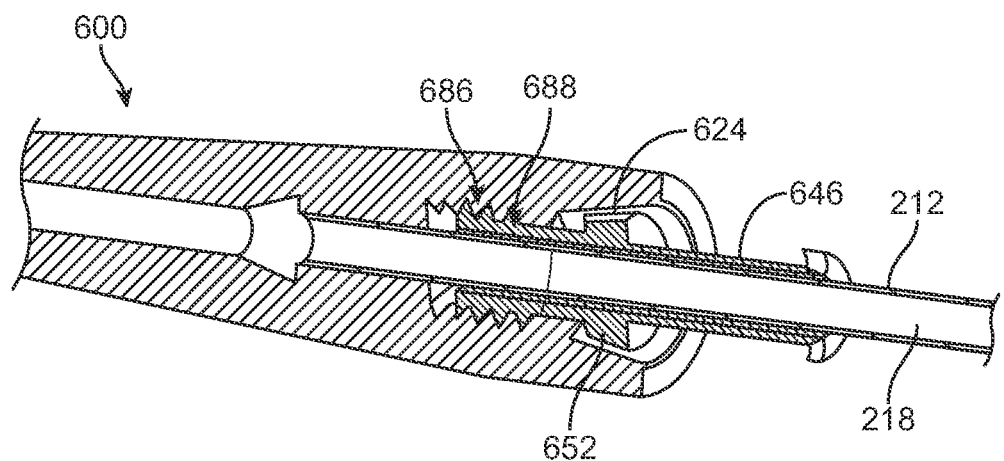
FIG. 6A is a sectional view taken along line A-A of FIG. 6, with cables and the stent-graft prosthesis removed from the stent-graft delivery system for illustrative purposes only.
Figure 6B:
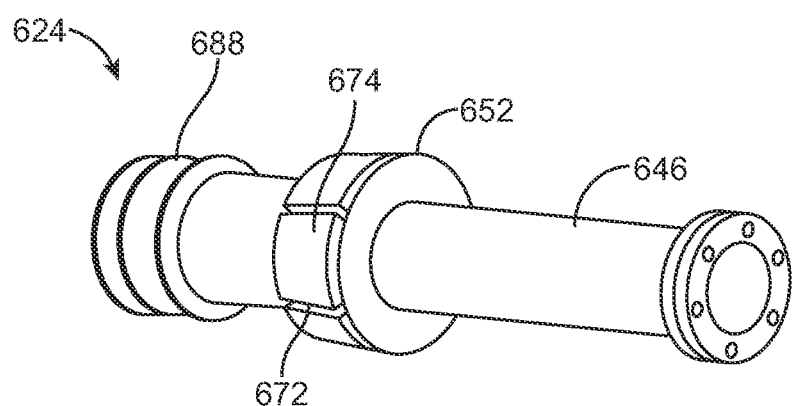
FIG. 6B is a perspective view of a guiding assembly of FIG. 6 removed from the stent-graft delivery system for illustrative purposes only.

FIGS. 6-8 illustrate a distal portion of a delivery system 600 according to another embodiment hereof including a tip capture mechanism having a plurality of cables that allow for partial or gradual deployment and repositioning of a stent-graft prosthesis. In this embodiment, the cables extend over rather than loop around the endmost crowns of the stent-graft prosthesis in order to selectively constrain the crowns and couple the stent-graft prosthesis to the delivery system. In FIGS. 6-8, only proximal end stent 240A of stent-graft prosthesis 230 is shown for purposes of illustration only but it will be understood by those of ordinary skill in the art that delivery system 600 is configured to deliver and deploy a stent-graft prosthesis such as but not limited to stent-graft prosthesis 230. FIG. 6 illustrates proximal end stent 240A in a compressed delivery configuration, FIG. 7 illustrates endmost crowns 242A of proximal end stent 240A in a partially deployed or radially expanded configuration but still captured via the tip capture mechanism, and FIG. 8 illustrates the position of the guiding assembly after the cables are removed and endmost crowns of the stent-graft prosthesis are released from the tip capture mechanism. FIG. 6A illustrates a sectional view taken along line A-A of FIG. 6 with the cables and the stent-graft prosthesis removed from the stent-graft delivery system for illustrative purposes only, while FIG. 6B illustrates the guiding assembly removed from the delivery system for illustrative purposes only.

Similar to delivery system 200, delivery system 600 includes an elongate inner shaft 612 having a distal tip assembly 628 coupled to a distal end 616 thereof, a plurality of elongate cables 626 that releasably couple proximal end stent 240A to delivery system 600, a guiding assembly 624 sliding disposed over inner shaft 612 for guiding and directing cables 626, and an outer sheath or graft cover 602 which retains stent-graft prosthesis 230 in a constrained or compressed diameter configuration while the delivery system is tracked through a body lumen to the deployment site. Inner shaft 612 is similar to inner shaft 212 described above, and graft cover 602 is similar to graft cover 202 described above. However, in this embodiment, guiding assembly 624 includes a shaft 646 slidingly disposed over inner shaft 612 and an anvil or guiding component 652 formed or disposed over a distal end 656 of shaft 646. Shaft 646 is a relatively short shaft which extends from at least endmost crowns 242A to distal tip assembly 628. An inner surface of a tubular sleeve portion 660 of distal tip assembly 628 may include threads 686 that mate with threads 688 on an outer surface of guiding component 652. Threads 686, 688 are continuous helical ridges that wrap around an outer surface of an inner surface of sleeve portion 660 and an outer surface of guiding component 652, respectively, to form a matched or mating pair of threads. As will be understood by those of ordinary skill in the art, threads 686, 688 are used to convert rotational to translational or linear movement as will be explained in more detail herein.

Each cable 626 is an elongated strand of material that extends from a proximal end of delivery system 600 over inner shaft 612, over shaft 646, extends over or around endmost crowns 242A of stent-graft prosthesis 230, and within longitudinal grooves 672 formed on an inclined or tapered outer surface 674 of guiding component 652. In a first relative position of guiding assembly 624 and distal tip assembly 628 depicted in FIG. 6, tubular sleeve portion 660 of distal tip assembly 628 extends over guiding component 652 and thereby constrains distal ends 668 of cables 626 as will be described in more detail herein.

More particularly, distal ends 668 of cables 626, which include balls or spheres 680 attached thereto or integrally formed therewith, are received within an annular channel or groove 684 formed on tapered outer surface 674 of guiding component 652. Distal ends 668 of cables 626 are constrained or wedged within a space 682 formed between tapered outer surface 674 of guiding component 652 and a corresponding tapered inner surface of sleeve portion 660 of distal tip assembly 628. Spheres 680 have a diameter greater than the diameter or width of cables 626, and the diameter of spheres 680 is greater than the width of longitudinal grooves 672 so that the spheres cannot pass through the longitudinal grooves of the guiding component. Accordingly, the distal ends of cables 626 are wedged or secured between guiding component 652 and distal assembly 628, and an intermediate portion 670 of cables 626 cover and constrain endmost crowns 242A of stent-graft prosthesis 230. Tension is applied to the proximal ends of cables 626 in order to hold cables 626 generally straight or taut over endmost crowns 242A, thereby pulling or constraining the endmost crowns towards or against guiding assembly 624.

When initial or partial deployment of prosthesis 630 is desired, graft cover 602 is partially retracted to allow the body of the prosthesis to self-expand as described above with respect to FIGS. 3 and 3A. At least a portion of the body of the stent-graft prosthesis expands while the endmost crowns remain covered and constrained by intermediate portions 670 of cables 626. With distal tip assembly 628 and guiding assembly 624 still in the first relative position in which sleeve portion 660 of distal tip assembly 628 extends over guiding component 652 to constrain distal ends 668 of cables 626, tension on cables 626 may be selectively adjusted to allow for gradual continuous radial expansion and/or contraction of endmost crowns 242A of stent-graft prosthesis 230. More particularly, with reference to FIG. 7, endmost crowns 242A of stent-graft prosthesis 230 are radially expanded or deployed in a continuous gradual manner by reducing tension on cables 626. Intermediate portions 670 of cables 626 still extend over or cover endmost crowns 242A but the endmost crowns are no longer pulled against guiding assembly 624. Rather, by reducing the tension of cables 626, endmost crowns 242A are permitted to radially self-expand and the endmost crowns are radially spaced apart from guiding assembly 624 of delivery system 600. If any repositioning is desired, endmost crowns 242A may be radially contracted towards or back to the position shown in FIG. 6 by increasing the tension of cables 626. Although not required, tapered outer surface 674 of guiding component 652 assists to secure distal ends 668 of cables 626 between guiding component 652 and tubular sleeve 660. In addition to the enlarged relative dimension of spheres 680, tapered outer surface 674 prevents distal ends 668 of cables 626 from unintentionally sliding out of longitudinal grooves 672 when tension of cables 626 is varied or adjusted to selectively expand or contract proximal end stent 240A.

After any and all repositioning is performed and stent-graft prosthesis 630 is positioned as desired, endmost crowns 242A of stent-graft prosthesis 230 may be fully deployed and released from delivery system 600 via rotation of distal assembly 628. In order to fully deploy the stent-graft prosthesis, inner shaft 612 and distal tip assembly 628 coupled thereto are rotated or turned. Stated another way, distal tip assembly 628 is coupled or attached to inner shaft 612 such that rotation of the shaft also rotates the distal tip assembly (i.e., they are not rotatable relative to each other). When inner shaft 612 and distal tip assembly 628 are rotated, guiding assembly 624 is prevented from rotation due to cables 626 being pinned or held within grooves 672, 684 of guiding component 652. In another embodiment hereof (not shown), shaft 646 may be elongated to extend to a proximal end of the delivery system and a proximal end of shaft 646 may be held stationary to prevent guiding assembly 624 from rotation. Because guiding assembly 624 is prevented from rotating, the rotational movement of distal tip assembly 628 is converted to translational or linear movement of guiding assembly 624 in a proximal direction relative to distal tip assembly 628 due to the threaded relationship between distal tip assembly 628 and guiding component 652. Rotation of inner shaft 612 continues until distal tip assembly 628 and guiding assembly 624 are in a second relative position shown in FIG. 8 in which sleeve portion 660 of distal tip assembly 628 does not constrain distal ends 668 of cables 626. Stated another way, rotation of inner shaft 612 continues until distal ends 668 of cables 626 are proximal to a proximal end of distal tip assembly 628. Sleeve portion 660 is retracted to expose at least a portion of annular groove 684 having balls 680 received thereof, at which point distal ends 668 of cables 626 may be released or unconstrained via space 682 formed between tapered outer surface 674 of guiding component 652 and the corresponding tapered inner surface of sleeve portion 660 of distal tip assembly 628. When distal ends 668 of cables 626 are no longer constrained, intermediate portions 670 of cables 626 may be released or removed from endmost crowns 242A of stent-graft prosthesis 230. As such, the stent-graft prosthesis is no longer coupled to delivery system 600 and the delivery system may then be removed from the patient, leaving stent-graft prosthesis 230 deployed in situ.

Although the embodiment of FIGS. 6-8 is shown and described with relative movement of guiding assembly 624 and distal tip assembly 628 being accomplished via rotation of inner shaft 612, it will be understood by those of ordinary skill in the art that other structural relationships rather than mating threads 686, 688 may be utilized to result in relative movement between guiding assembly 624 and distal tip assembly 628. For example, in another embodiment (not shown), shaft 646 may be an elongated shaft that extends over inner shaft 612 to a proximal end of delivery system 600 and the elongated shaft 646 may be proximally retracted in order to fully deploy the stent-graft prosthesis. Alternatively, inner shaft 612 and distal tip assembly 628 coupled thereto may be distally advanced within the elongated shaft 626 in order to accomplish relative movement between guiding assembly 624 and distal tip assembly 628.

In addition, although embodiments hereof depict stent-graft prosthesis 230 has an open-web or free-flow proximal end configuration, the delivery systems described herein may be utilized with stent-grafts having various configuration. The open web proximal end configuration allows blood flow through endmost crowns 242A for perfusion during and/or after implantation. As utilized herein, "endmost crowns" refers to the most proximal crowns or peaks of the stent-graft prosthesis, regardless of whether or not the crowns are coupled to the graft material or whether the crowns extend beyond the edge of the graft material. More particularly, first end stent 240A is attached to graft 232 so that endmost crowns 242A thereof extend past or beyond the graft material such that the endmost crowns are exposed or bare. Alternatively, stent-graft prosthesis 230 may have a proximal closed web configuration. In a closed web configuration, the endmost crowns do not extend past or beyond the graft material but rather are covered by graft material. In some cases a closed web configuration may be required or chosen due to application, i.e., a thoraric aortic aneurysm rather than an abdominal aortic aneurysm, and/or user preferences. If delivery systems described herein are utilized with a stent-graft prosthesis having a closed web configuration, cables 226/626 may be threaded between the graft material and crowns or may pass through the graft material. In addition, in the above embodiments, the scaffolding or support of the stent-graft prostheses have been illustrated as a series of independent or separate self-expanding stents/sinusoidal patterned rings. However, as will be understood by one of ordinary skill in the art, the support structure or scaffolding of a stent-graft prosthesis may have other configurations such as a series of sinusoidal patterned rings coupled to each other to form a self-expanding stent, or a helical stent or series of helical stents. In another embodiment, the support structure or scaffolding of a stent-graft prosthesis may be a unitary tubular component such as but not limited to a laser cut tubular stent.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent-graft delivery system comprising:
an elongate shaft;
a plurality of elongate cables, wherein each cable extends over the elongate shaft and includes a first end, an intermediate portion configured to engage endmost crowns of a stent of a stent-graft prosthesis, and a second end that extends distally beyond the stent-graft prosthesis;
a guiding assembly disposed over the elongate shaft;
a distal tip assembly coupled to a distal end of the elongate shaft, the distal tip assembly and the guiding assembly being moveable relative to each other, wherein a portion of the distal tip assembly extends proximally over an outer surface of a distal portion of the guiding assembly and constrains the second ends of the cables between the outer surface of the distal portion of the guiding assembly and an inner surface of the portion of the distal tip assembly in a first relative position of the distal tip assembly and the guiding assembly and wherein the distal tip assembly does not constrain the second ends of the cables in a second relative position of the distal tip assembly and the guiding assembly,
wherein, in the first relative position of the distal tip assembly and the guiding assembly, tension on the cables can be selectively reduced for gradual continuous expansion of the endmost crowns of the stent or can be selectively increased for gradual continuous radial contraction of the endmost crowns of the stent.

2. The stent-graft delivery system of claim 1, wherein the guiding assembly includes an elongated multi-lumen shaft and each cable extends through one of a plurality of lumens defined by the multi-lumen shaft.

3. The stent-graft delivery system of claim 2, wherein an annular stop is coupled to an outer surface of the multi-lumen shaft and the intermediate portions of the cables are configured to loop around the endmost crowns to pull the stent against the annular stop.

4. The stent-graft delivery system of claim 3, wherein the distal tip assembly moves relative to the guiding assembly.

5. The stent-graft delivery system of claim 4, wherein the distal tip assembly moves in a distal direction relative to the guiding assembly and the second ends of the cables are proximal to a proximal end of the distal tip assembly when the guiding assembly and the distal tip assembly are in the second relative position.

6. The stent-graft delivery system of claim 1, wherein the guiding assembly includes a guiding component and each cable extends through grooves formed on an outer surface of a tapered distal portion of the guiding component, and the intermediate portions of the cables are configured to extend over and cover the endmost crowns of the stent of the stent-graft prosthesis.

7. The stent-graft delivery system of claim 6, wherein the guiding assembly moves relative to the distal tip assembly.

8. The stent-graft delivery system of claim 7, wherein the guiding assembly moves in a proximal direction relative to the distal tip assembly and the second ends of the cables are proximal to a proximal end of the distal tip assembly when the guiding assembly and the distal tip assembly are in the second relative position.

9. The stent-graft delivery system of claim 8, wherein an inner surface of the distal tip assembly includes threads that mate with threads on an outer surface of the guiding assembly and wherein rotation of the elongate shaft rotates the distal tip assembly and results in longitudinal movement of the guiding assembly.

10. The stent-graft delivery system of claim 1, further comprising:
    a retractable outer sheath defining a lumen, wherein the elongate shaft is slidingly received within the lumen of the outer sheath; and
    a self-expanding stent-graft prosthesis disposed over the elongate shaft, proximal to the distal tip assembly, wherein the stent-graft prosthesis includes a radially-compressible stent coupled to a tubular graft and the intermediate portions of the cables selectively constrain endmost crowns of the stent.

11. The stent-graft delivery system of claim 1, wherein the plurality of cables are elongate strands of a first diameter and the second ends of the cables are a second diameter which is greater than the first diameter.

12. A stent-graft delivery system comprising:
    an elongate shaft;
    a self-expanding stent-graft prosthesis disposed over the elongate shaft, wherein the stent-graft prosthesis includes a radially-compressible stent coupled to a tubular graft;
    a plurality of elongate cables, wherein each cable extends over the elongate shaft and includes a first end and a second end that extends distally beyond the stent-graft prosthesis;
    a guiding assembly disposed over the elongate shaft, wherein a distal portion of the guiding assembly is configured to receive the second ends of the cables;
    a distal tip assembly coupled to a distal end of the elongate shaft, the distal tip assembly and the guiding assembly being moveable relative to each other,
    wherein, in a first relative position of the distal tip assembly and the guiding assembly, a proximal portion of the distal tip assembly extends over an outer surface of the distal portion of the guiding assembly to temporarily constrain the second ends of the cables and an intermediate portion of each cable constrains an endmost crown of the stent, whereby tension on the cables can be selectively adjusted to allow for both gradual continuous radial expansion and contraction of the endmost crowns of the stent, and
    wherein, in a second relative position of the distal tip assembly and the guiding assembly, the proximal portion of the distal tip assembly does not extend over an outer surface of the distal portion of the guiding assembly, the distal tip assembly does not constrain the second ends of the cables, and the intermediate portion of each cable does not constrain an endmost crown of the stent.

* * * * *